United States Patent [19]

Zaiger et al.

[11] Patent Number: Plant 7,475

[45] Date of Patent: Mar. 19, 1991

[54] NECTARINE TREE "ZEE GRAND"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95351

[21] Appl. No.: 471,977

[22] Filed: Jan. 29, 1990

[51] Int. Cl.[5] ..... A01H 5/00

[52] U.S. Cl. ..... Plt./41

[58] Field of Search ..... Plt./41

*Primary Examiner*—James R. Feyrer

[57] ABSTRACT

A new and distinct variety of nectarine tree with the following unique combination of desirable features:

1. Early maturity of the fruit.
2. Relative uniform size of fruit throughout the tree.
3. Fruit with an attractive red skin color.
4. Heavy and regular production.
5. Fruit with firm flesh, good flavor and eating quality.
6. The fruit having the ability to ship to long distance markets.

1 Drawing Sheet

ORIGIN OF THE VARIETY

The present variety of nectarine tree was originated by us in the experimental orchard located near Modesto, Calif. as a third generation seedling from a cross between Red Grand Nectarine (U.S. Plant Pat. No. 1,060) and Royal Gold Peach (U.S. Plant Pat. No. 2,663). A large group of these seedlings were grown and maintained under careful observation by us and one such seedling which is the present variety evidenced distinctive desirable characteristics with respect to its fruit, was selected for asexual reproduction and commercialization.

ASEXUAL REPRODUCTION OF THE VARIETY

The new and distinct variety of nectarine tree was asexually reproduced by budding in the experimental orchard located near Modesto, Calif. and shows that all said characteristics come true to the original tree and are established and transmitted through succeeding propagations.

SUMMARY OF THE VARIETY

A new and distinct variety of nectarine tree which is of large size, medium dense, vigorous upright growth and is a regular and productive bearer of medium to large, firm, yellow flesh, clingstone fruit with good flavor and eating quality. The fruit is further characterized by sizing relatively uniform throughout the tree, being nearly globose in shape with a high degree, of attractive red skin color. The fruit maturing 2 to 3 days before May Grand Nectarine (U.S. Plant Pat. No. 2,794), and the tree having the ability to produce a greater number of larger size fruit.

PHOTOGRAPHS OF THE VARIETY

The accompanying photographic illustrations show typical specimens of the foliage and fruit of the new nectarine variety with the upper and lower surface of the leaves being illustrated; an exterior and sectional view of the fruit being divided on its suture plane to reveal flesh coloration and showing a stone remaining in place. The photographic illustrations were taken shortly after being picked at maturity (firm ripe) and the colors are as nearly true as reasonably possible in a color representation of this type.

DESCRIPTION OF THE VARIETY

The following is a detailed botanical description of the new and distinct variety of nectarine tree, its flowers, foliage and fruit based on observations of specimens grown at Modesto, Calif., with color definitions (except those in common terms) referenced to Reinhold Color Atlas, by A. Kornerup and J. H. Wanscher.

Tree:
- *Size.*—Large.
- *Vigor.*—Vigorous.
- *Form.*—Upright.
- *Density.*—Medium dense.
- *Productivity.*—Productive.
- *Bearer.*—Regular.

Trunk:
- *Size.*—Medium stocky.
- *Texture.*—Medium shaggy.
- *Color.*—Brown to grayish brown.

Branches:
- *Size.*—Medium to large.
- *Texture.*—Smooth to medium rough.
- *Lenticels.*—Medium number. Small size.
- *Color.*—Reddish brown to brown.

Leaves:
- *Size.*—Large. Average length — 6½". Average width — 1½".
- *Form.*—Lanceolate. Pointed.
- *Margin.*—Crenate.
- *Texture.*—Smooth.
- *Thickness.*—Medium.
- *Petiole.*—Medium length. Medium thickness.
- *Glands.*—Reniform. Number varies from 1 to 4. Average number 2. Medium to large size.
- *Color.*—Upper surface — green to dark green (27-F-6) to (27-F-8). Lower surface — grayish green to dull green (28-E-6) to (28-E-7).

Flower buds:
- *Size.*—Medium to large.
- *Form.*—Plump.
- *Pubescense.*—Pubescent.

Flowers:
- *Size.*—Large — showy.
- *Pollen.*—Present.
- *Color.*—Pink.

*Blooming period.*—Mar. 2, 1988 to Mar. 8, 1988 Varies slightly with climatic conditions.

Fruit:

*Maturity when described.*—Firm ripe.

*Size.*—Medium to large. Average diameter axially — 2½" to 2⅞". Average transversely in suture plane — 2½" to 2⅞".

*Date of first picking.*—June 10, 1988.

*Date of last picking.*—June 15, 1988.

*Form.*—Globose — nearly symmetrical.

*Suture.*—Shallow — extends from base to apex.

*Ventral surface.*—Nearly round — very slightly lipped.

*Apex.*—Round to slight point.

*Base.*—Retuse.

*Cavity.*—Rounded — slightly elongated in suture plane. Average depth — 7/16". Average width — ¾".

Skin:

*Thickness.*—Medium.

*Texture.*—Tough — tenacious to flesh.

*Tendency to crack.*—None.

*Down.*—Wanting.

*Color.*—Bright yellow ground color (4-A-7) to (4-A-8). Overspread with red (9-A-8) to (10-B-8).

Flesh:

*Texture.*—Firm — meaty.

*Fibers.*—Tender — moderate number.

*Ripens.*—Evenly.

*Flavor.*—Mild.

*Juice.*—Moderate.

*Aroma.*—Very little.

*Flavor.*—Good — sub-acid to mild.

*Eating quality.*—Good.

*Color.*—Yellow to chrome yellow (4-A-8) to (5-A-7).

Stone:

*Type.*—Clingstone.

*Size.*—Large. Average length — 1 7/16". Average width — 1". Average thickness — ¾".

*Form.*—Ovid.

*Base.*—Straight to slightly oblique.

*Apex.*—Acuminate.

*Sizes.*—Equal to unequal.

*Surface.*—Irregularly furrowed toward apex, pitted toward base.

*Tendency to split.*—Slight.

*Color.*—Light brown (7-B-5) to (7-C-5).

Use: Dessert.

*Market.*—Local and long distance.

Keeping quality: Good.

Shipping quality: Good.

The present variety of nectarine tree and its fruit may vary in slight detail due to cultural practices, soil and climatic conditions under which the variety may be grown; the present description is that of the variety grown under the ecological conditions prevailing at Modesto, Calif.

We claim:

1. A new and distinct variety of nectarine tree, substantially as illustrated and described, characterized by its large size, vigorous, upright growth and a regular and productive bearer of early maturing, medium to large, firm, yellow flesh, clingstone fruit with good flavor and eating quality; the tree is further characterized by bearing fruit that are relatively uniform in size throughout the tree with a high degree of attractive red skin color and when compared to May Grand Nectarine (U.S. Plant Pat. No. 2,794) matures 2 to 3 days earlier and producing a greater number of larger size fruit.

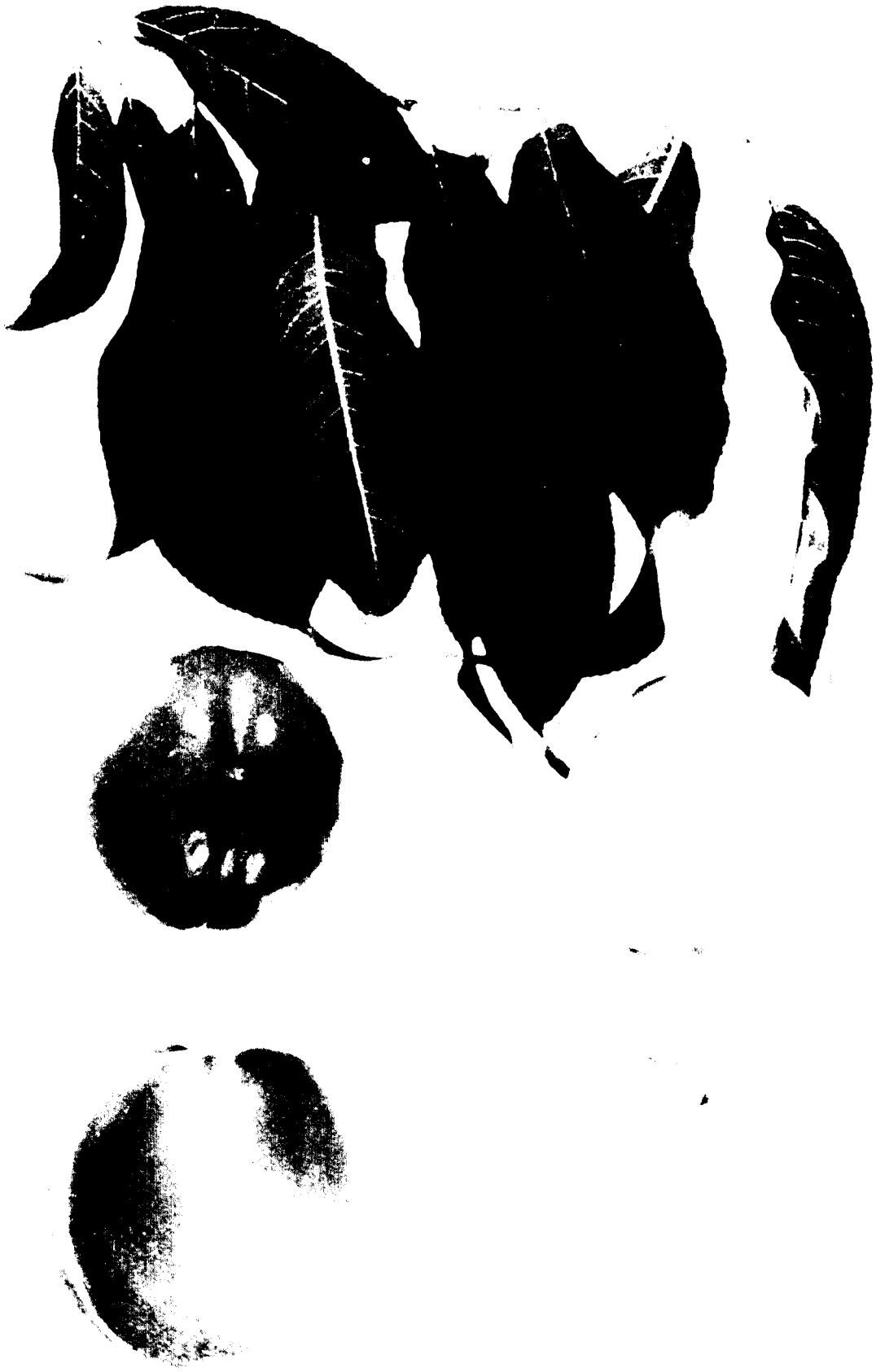

* * * * *